United States Patent
Derr (10) Patent No.: US 7,318,273 B2
(45) Date of Patent: Jan. 15, 2008

(54) METHOD FOR PRODUCING PH PROBES

(75) Inventor: Andreas Derr, Wutöschingen (DE)

(73) Assignee: Testo AG, Lenzkirch (DE)

( * ) Notice: Subject to any disclaimer, the term of this patent is extended or adjusted under 35 U.S.C. 154(b) by 448 days.

(21) Appl. No.: 10/511,420

(22) PCT Filed: Jun. 25, 2003

(86) PCT No.: PCT/EP03/06715

§ 371 (c)(1),
(2), (4) Date: Oct. 14, 2004

(87) PCT Pub. No.: WO2004/015408

PCT Pub. Date: Feb. 19, 2004

(65) Prior Publication Data

US 2005/0179438 A1 Aug. 18, 2005

(30) Foreign Application Priority Data

Jul. 25, 2002 (DE) ................................. 102 33 903

(51) Int. Cl.
*H01R 43/00* (2006.01)
*H05K 13/00* (2006.01)
(52) U.S. Cl. ............................. 29/854; 29/830; 29/858; 29/592.1; 29/593; 204/408; 204/420; 205/787.5
(58) Field of Classification Search ............... 29/592.1, 29/593, 595, 825, 830, 831, 854, 858; 204/408, 204/420, 433, 435, 422, 412; 205/787.5, 205/789; 324/438; 422/82.01, 82.12
See application file for complete search history.

(56) References Cited

U.S. PATENT DOCUMENTS

| 3,415,731 A | 12/1968 | Carter |
| 3,444,067 A | 5/1969 | Watanabe et al. |
| 3,455,793 A * | 7/1969 | Buzza et al. ............. 205/787.5 |
| 3,523,777 A | 8/1970 | Petersen et al. |
| 3,965,383 A | 6/1976 | List et al. |
| 4,004,331 A | 1/1977 | List et al. |

(Continued)

FOREIGN PATENT DOCUMENTS

DE          25 44 360           4/1976

(Continued)

*Primary Examiner*—Minh Trinh
*Assistant Examiner*—Donghai D. Nguyen
(74) *Attorney, Agent, or Firm*—Muirhead and Saturnelli, LLC (57) ABSTRACT

A method for producing a pH measuring probe includes: providing an electrode wire protruding out of both sides of a recording device, the electrode wire being fixed to the recording device with the first end thereof, placing a glass tube over a second end of the electrode wire until reaching a cavity of the recording device, the glass tube and the recording device being fixed together; providing another electrode wire protruding from both sides of a base plate including a recess for the recording device, the other electrode wire being fixed to the base plate with its end protruding; providing a casing comprising first and second openings, the casing and base plate being sealed together, forming the housing; and guiding the glass tube through the recess in the base plate until it protrudes out of an opening in the casing and the recording device is inserted into the base plate.

33 Claims, 7 Drawing Sheets

U.S. PATENT DOCUMENTS

| | | |
|---|---|---|
| 4,008,141 A | 2/1977 | Kotani et al. |
| 4,012,308 A * | 3/1977 | Jerrold-Jones et al. ...... 204/420 |
| 4,128,468 A * | 12/1978 | Bukamier .................... 204/420 |
| 4,162,211 A * | 7/1979 | Jerrold-Jones ............... 204/420 |
| 4,167,300 A | 9/1979 | Fischer et al. |
| 4,252,124 A | 2/1981 | Maurer et al. |
| 4,783,250 A | 11/1988 | Pons et al. |
| 4,959,138 A | 9/1990 | Brinkmann et al. |
| 6,495,012 B1 * | 12/2002 | Fletcher et al. ............. 204/435 |
| 7,017,256 B2 * | 3/2006 | Joly et al. ..................... 29/858 |

FOREIGN PATENT DOCUMENTS

| | | |
|---|---|---|
| DE | NR. 359 750 | 4/1980 |
| DE | NR. 375 190 | 10/1981 |
| DE | 34 05 431 C2 | 3/1985 |
| DE | 36 17 479 A1 | 11/1987 |
| DE | 100 04 583 A1 | 8/2001 |
| DE | 100 53 979 A1 | 5/2002 |
| EP | 0 247 535 A2 | 12/1987 |
| GB | 2 370 646 A | 7/2002 |

\* cited by examiner

METHOD FOR PRODUCING PH PROBES

FIELD OF THE INVENTION

The present invention relates to a method for producing a pH probe.

BACKGROUND OF THE INVENTION

Such probes may be, for example, pH measuring probes for measuring the pH of a liquid or food, such as meat, and they may be installed in portable measuring devices. In the simplest embodiment, such measuring probes have two electrodes in a housing. A chamber holding a second electrode formed by a polymer protolyte gel, for example, is usually provided between the first electrode and the housing.

In manufacturing such measuring probes, it is important for the inner electrode to have a high resistance in comparison with the outer electrode, and the amount of measuring liquid exchange between the liquid in the first electrode and the liquid in the second electrode should be minimized. Essentially two different designs are known for such polymer electrolyte measuring probes. First, there are measuring probes made completely of glass, and second, there are also measuring probes made of plastic but with the inner electrode situated in a glass tube. The design and functioning of this electrode are explained briefly below.

In the manufacture of glass electrodes, two electrode chambers are first produced by glass blowing, with the inner electrode being sealed by a pH glass diaphragm and the outer electrode being situated in an electrode chamber which is fused onto the closed end of the inner electrode. This results in a kind of double-walled glass beaker design.

A liquid electrolyte is cast into the chamber of the inner electrode. The inner chamber is sealed using a foam cylinder which seals the inner chamber like a plug, and a silver wire is passed through the foam cylinder until reaching the electrode bottom. To further seal the inner chamber, silicone is extruded into the rear area of the glass tube. Measuring probes preassembled in this way must then cure for a couple of hours to secure the silver wire in the inner chamber.

The silver wire of the inner electrode is then connected to a coaxial line; for shielding reasons, it is important for the soldered end of the silver wire together with the inner insulation of the coaxial line to be immersed in the glass tube of the inner electrode. Because of the small diameter of the glass tube, soldering cannot be performed inside the glass tube, so a coil in the form of a mechanical spring or spiral must typically be coiled at the end of the silver wire protruding out of the glass tube. After soldering, this coil, which forms the end of the silver wire, is compressed by the insulation on insertion of insulation.

The chamber of the outer electrode is closed using foam and sealed by a silicone material in the same way. A plastic cap is pushed onto the end of the probe for tensile strain relief of the electrode rod and the cap is cast there using an adhesive, typically a two-component epoxy resin. A polymer electrolyte is added to the outer chamber of the measuring probe under a vacuum.

Such glass electrodes are extremely expensive to manufacture because of the multitude of different manufacturing steps. Another problem is that, because of the material of the glass electrode and the small amount of space available, a great many complicated manufacturing steps are necessary during assembly of the glass electrode, hardly allowing adequate yield in automated production. The use of glass tubes in particular is problematical here because the various components are frequently assembled inside the fragile glass electrodes or at least in their immediate proximity. In most cases, this prevents the use of manufacturing machines for automation of the manufacturing process. However, at the same time, this also means that because of the plurality of different manufacturing steps and the need for performing them manually for the most part, the corresponding glass measuring probes are very expensive to manufacture.

Meanwhile, there is thus a demand for providing measuring probes for measuring instruments which are simpler and thus less expensive to manufacture without restricting their functionality.

Plastic measuring probes are far more easily manufactured than the measuring probes made of glass as described above. The design of one such plastic measuring probe is described in DE 100 04 583 C2, for example.

The manufacturing steps required for producing such plastic probes are essentially the same as those for producing a measuring probe of glass. Some of the manufacturing steps may be simplified by automation because first of all, the glass sheathing of the electrode need no longer be produced by glass blowing, which is very expensive. Nevertheless it is also necessary here to perform a number of manufacturing steps which have the unwanted effect of making the plastic measuring probe more expensive.

As already described in DE 100 04 583 C2, plastic probes are much sturdier than glass probes, but they are very sensitive to impact, in particular in the axial direction. In addition, it is necessary from an economic standpoint in particular to occasionally refill or replace the electrolyte liquid inside the measuring probe. However, in the case of measuring probes made of plastic, this is possible only to an unsatisfactory extent or not at all. In addition, glass measuring probes are characterized in comparison with plastic measuring probes in that they may be used even when high hygienic demands must be met or when the medium to be measured has a very high temperature, for example. In some cases, glass probes are much better than plastic measuring probes because of the low outgassing of impurities and because of their high thermal stability.

Accordingly, it is desirable to manufacture high-quality measuring probes without using gluing or casting methods, if possible. Further, it is desirable to provide the simplest possible method for manufacturing high-quality probes that is suitable for automation. Yet further, it is desirable to create a method for manufacturing a measuring probe which makes it possible to open the measuring probe again after being manufactured.

SUMMARY OF THE INVENTION

According to one embodiment of the present invention, a method for manufacturing a measuring probe, in particular a pH measuring probe having a housing and two electrodes, by the following method steps is provided:

(a) in order to form a receptacle device, an electrode wire sheathed with extruded plastic protruding out of the receptacle device on both ends is provided; the electrode wire is secured at its first end on the receptacle device; in order to form the first electrode, a glass tube is pushed over a second end of the electrode wire until the glass tube is in contact with a recess in the receptacle device; the glass tube and the receptacle device are joined together;

(b) in order to form a base plate having a recess in the form of the receptacle device, another electrode wire sheathed with extruded plastic protruding out of the base plate on both ends is provided; the additional electrode wire is secured on the base plate at its end protruding out of the base plate;

(c) a sheathing having a first opening in the form of the base plate and a second opening in the form of the glass tube is provided; the sheathing and the base plate are joined to form the housing;

(d) the glass tube is passed through the recess in the base plate until the glass tube protrudes out of an opening in the sheathing and the receptacle device comes in contact with the base plate.

The idea on which the present invention is based is to run the silver wire for the inner electrode directly, i.e., without additional soldering and without providing an additional line, from the interior of the glass tube to the exterior and to secure it there. The silver wire is then prepared to form the outside contact of the measuring electrode. The particular advantage of the method according to this embodiment of the present invention is that it is no longer necessary to perform complex soldering of a line introduced from the outside or to twist the silver wire. Each electrode chamber is advantageously manufactured separately. Furthermore, the method according to this embodiment of the present invention makes a very high quality contact available which requires fewer processing steps than known manufacturing methods.

For final assembly, one electrode is simply inserted into the other, and the space is filled with an electrolyte.

Other advantageous embodiments and refinements of the present invention are evident from the subclaims and the description with reference to the drawing.

BRIEF DESCRIPTION OF THE DRAWINGS

The present invention is explained in greater detail below on the basis of the exemplary embodiments illustrated in the drawing.

DETAILED DESCRIPTION OF VARIOUS EMBODIMENTS

In all the figures, the same elements or elements having the same function are labeled with the same reference notation unless otherwise indicated.

Figure 1:
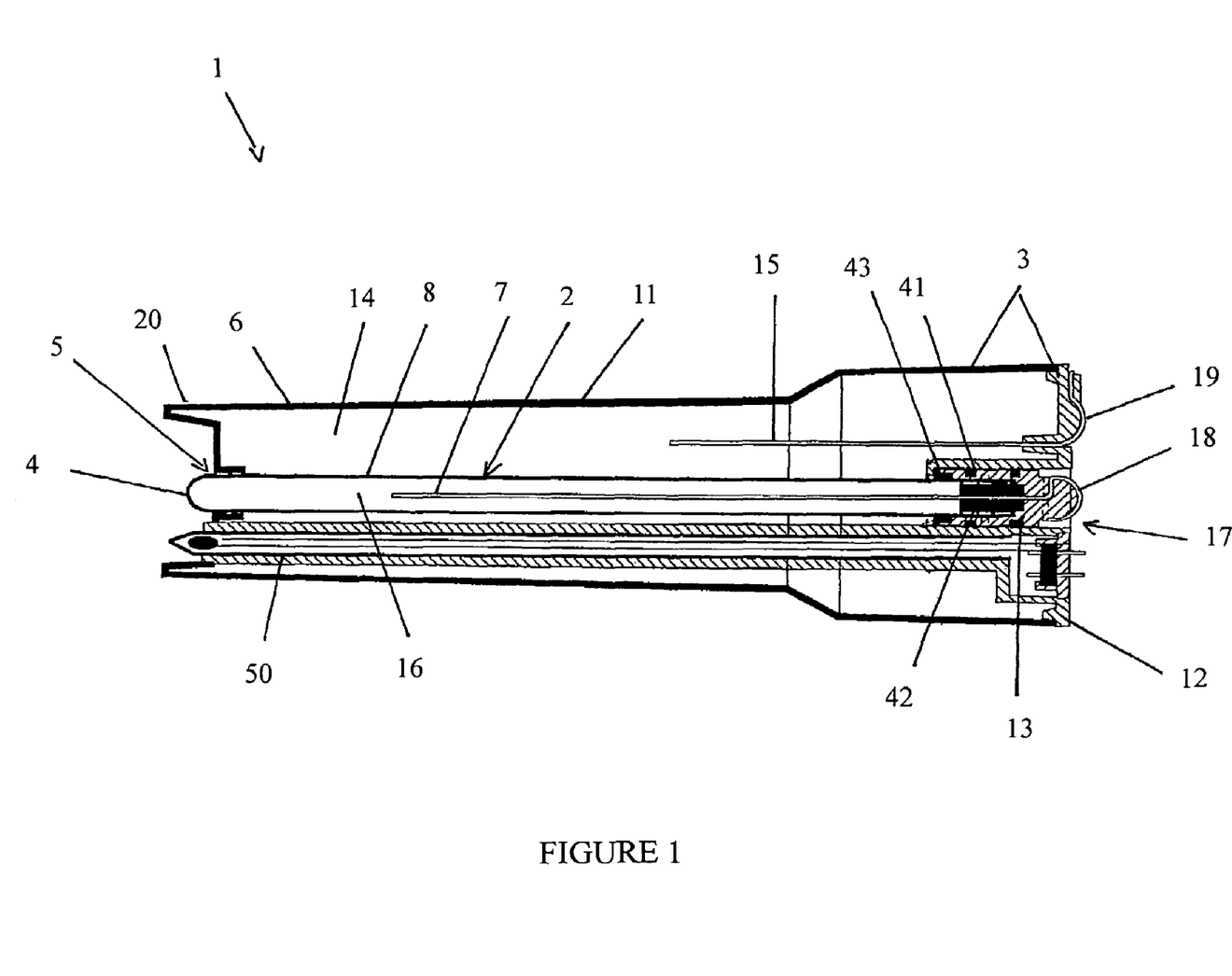
FIG. 1 shows a schematic cross-sectional diagram of a first measuring module.

FIG. 1 shows a measuring device 1 in a schematic cross-sectional diagram. Measuring device 1 is designed here as a pH measuring module for measuring the pH of liquids, foods, wastewater and the like. Measuring module 1 may be part of a measuring instrument not shown in FIG. 1 or it may be the measuring instrument itself. Measuring module 1 has an elongated first electrode 2 and a housing 3 which at least partially surrounds first electrode 2. A measuring tip 4 of the first electrode protrudes out of an opening 5 provided specifically for it on upper end 6 of housing 3.

Housing 3 is composed of a sheathing 11 and a base plate (carrier plate) 12. Sheathing 11 and base plate 12 are preferably made of a somewhat elastic plastic. Housing 3 is tightly sealed to the outside except for an inlet (not shown) for the measuring liquid and opening 5. Additionally or alternatively, housing 3 may also have a safety jacket (not shown) on its upper end 6, protecting measuring module 1 toward the outside, e.g., from mechanical stress, moisture or the like.

First electrode 2 contains a silver wire 7, which is partially gold plated in an advantageous embodiment and has a sheathing of glass forming a glass tube 8 surrounding silver wire 7 at least in the area of measuring tip 4. Glass tube 8 holds a conventional electrolyte fluid and is sealed to the outside. At its end 13 facing base plate 12, first electrode 2 is fixedly joined to base plate 12, e.g., by gluing, while its other end protrudes out of sheathing 11 in the area of measuring tip 4.

The areas between first electrode 2 and housing 3 define a chamber 14. Measuring module 1 also has a second electrode 15 designed as a silver electrode attached to base plate 12 and protruding into chamber 14. Chamber 14 is advantageously filled with a polymer protolyte solution. First electrode 2 thus forms the inner electrode, with second electrode 15 forming the outer electrode. Silver wire 7 of inner electrode 2 is thus situated in an inner chamber 16, with outer electrode 15 being situated in an outer chamber 14.

Base plate 12 has a recess 17 which accommodates first electrode 2. End 13 of first electrode 2 fits snugly into this recess 17 and is secured there by suitable means, e.g., sealing rings, locking devices, adhesives, etc.

Base plate 12 also has electric contact faces 18, 19 on its outside. First and second electrodes 2, 15 are electrically connected to these contacts 18, 19.

In addition, housing 3 has protective webs 20 for protecting measuring tip 4 on its upper end 6. Measuring tip 4 may be rounded for this reason. Measuring module 1 here is particularly suitable for measurements in liquids and therefore is advantageously used in laboratory measuring instruments.

In addition, FIG. 1 shows a tube 50 which extends to a measuring tip 4 and is fixedly connected at one end to base plate 12, protruding out of housing 3 in area 6 at the other end. This pointed tube 50 is typically made of stainless steel and has a temperature sensor for determining the temperature of the material to be measured.

A measuring module 1 according to FIG. 1 functions as follows.

To perform a measurement, measuring probe 1 is introduced into a material to be measured (not shown). Liquid of the material to be measured enters into the area between first electrode 2 and second electrode 15 using suitable devices (not shown here), e.g., a diaphragm in the opening area of measuring module 1. Depending on the pH of the material to be measured, a potential gradient that develops between electrodes 2 and 15 may be tapped at contacts 18, 19. The voltage thus tapped is a measure of the pH.

An advantageous method for manufacturing pH measuring module 1 according to FIG. 1 is described below with reference to subfigures 1 through 10 of FIG. 2. The numbering used below corresponds to the subfigures in FIG. 2:

1. A silver wire 7, gold plated in a rear area 7', is provided. Gold-plated area 7' of silver wire 7 is bent at an angle. Partially gold-plated silver wire 7 is placed in a mold (not shown) with the gold-plated side facing outward and a plastic material is extruded around it, thus forming receptacle device 23.
2. Receptacle device 23 is then placed in another mold to produce seals 41, 42, 43. To this end, receptacle device 23 has grooves 40 on its outside surface. An elastomer is extruded into these grooves 40 to form sealing projections 41. Receptacle device 23 also has a central recess 26 out of which silver wire 7 protrudes. In this area of recess 26 and at the upper end of recess 26, an elastomer is also extruded to form a rubber buffer 42 and an inside gasket 43.

3. On its end opposite recess 26, receptacle device 23 also has a groove 44 running on the outside surface of receptacle device 23. In this area of receptacle device 23, a transverse through bore 45 is also provided. To attach silver wire 7, it is pushed with its area 7' through transverse through bore 45 and pulled tightly, so that wire 7' is firmly in contact with groove 44.

4. A protruding end of silver wire 7 which protrudes out of transverse through bore 45 is cut off. Area 7" of silver wire 7 protruding out of recess 26 is chlorinated, preferably for 20 minutes.

5. A glass tube 8 is provided, forming first electrode 2. First an electrolyte liquid is placed in glass tube 8. Then glass tube 8 with its end open at one side is pushed into recess 26 of receptacle device 23. Glass tube 8 and receptacle device 23 are secured to one another through inside gasket 43 and rubber buffer 42 and the entire system is sealed to the outside. Silver wire 7 is pushed into inner chamber 16 of glass tube 8 with the electrolyte fluid contained therein.

6. Silver wire 15 of second electrode 15 and a stainless steel tube 50 for the temperature sensor are placed in another mold and a plastic is suitably extruded around them. This forms base plate 12. After extrusion, silver rod 15 and stainless steel pipe 50 protrude out of base plate 12. Then silver wire 15 with its end 15' protruding out of base plate 12 is chlorinated.

Stainless steel tube 50 is additionally or alternatively coated with a plastic 51 on its exterior surface.

7. In order to form the temperature sensor, a conventional heat transfer compound is placed into a tip of stainless steel tube 50. Then a twin-cable NTC wire 52 (negative temperature coefficient) is inserted into the interior of stainless steel tube 50. The two ends of NTC wire 52 protrude out of tube 50 on the side of base plate 12. In the area of base plate 12, a contact plate 52 is produced by extrusion. Base plate 12 therefore advantageously has a recess 54 into which contact plate 53 is tightly inserted or engaged. Contact plate 52 has two contact rods 55 which pass through contact plate 53 and are soldered to NTC wire ends 52 protruding out of it in an area facing stainless steel tube 50.

Silver wire 15 of second electrode 15 is threaded at its one end which protrudes out of base plate 12 into a receptacle device 53, e.g., an eye, provided specifically for this purpose in base plate 12. Silver wire 15 is thus secured there tightly. In addition, silver wire 15 forms a contact face 19 there. The protruding end of silver wire 15 is again cut off.

8. Sheathing 11 of measuring probe 1 is manufactured by extrusion in a suitably designed mold. Then base plate 12 along with the temperature sensor and second electrode 15 is pushed into interior 14 of sheathing 11. The end of sheathing 11, which is open toward the outside, is then welded to the corresponding areas of base plate 12, e.g., by ultrasound, thereby sealing it. A double weld 57, 58 which is advantageously provided here should prevent the polymer protolyte liquid from subsequently flowing out. Enlarged subfigures (8a)-(8c) show a corresponding welding method for producing the two welds 57, 58 in three steps.

Alternatively it would of course also be possible to use other joining methods—such as a latching joint, a thread or the like, although ultrasonic welding combined with a double weld 57, 58 (see (8a)-(8c)) is a particularly preferred method.

9. Base plate 12 has an opening 17 through which first electrode 2 is insertable and receptacle device 23 may be inserted in a form-fitting manner. Electrode 2 together with receptacle device 23 is pushed through this opening 17 until first electrode 2 protrudes out of opening 5 of sheathing 11 on the other end of housing 3. Sealing projections 41 arranged in outside grooves 40 of receptacle device 23 ensure that first electrode 2 and/or receptacle device 23 will be sealed in recess 17 in base plate 12 provided for this purpose.

10. After inserting first electrode 2 together with base plate 12, a groove 60 is formed between receptacle device 23 and base plate 12 in an outer area of recess 17. First an O-ring 61 is inserted into this groove 60 for sealing purposes. Then a fixation/adjusting screw 62 is screwed into a thread provided for this purpose in base plate 12 or receptacle device 23. Alternatively, it would also be conceivable to provide a different type of sealing means, e.g., a latching means, instead of fixation/adjusting screw 62.

11. Finally, the polymer protolyte solution is added to outer chamber 14 through an opening (not shown in FIG. 2) provided for this purpose in housing 3 of measuring module 1.

Figure 3:
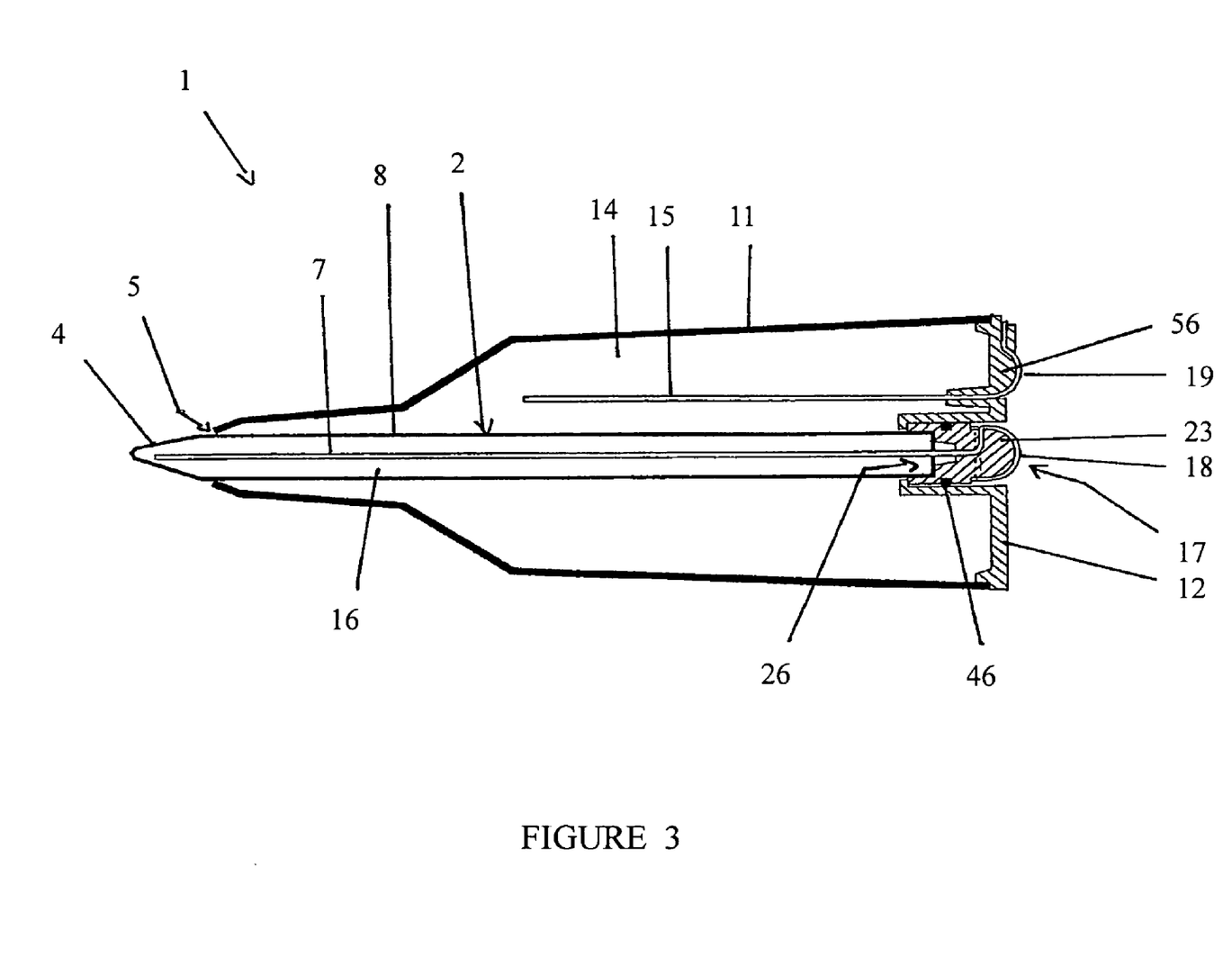
FIG. 3 shows a schematic cross-sectional diagram of a second measuring module.

FIG. 3 shows a second example of a measuring module 1 manufactured according to the present invention. In contrast with the exemplary embodiment in FIG. 1, measuring module 1 in FIG. 3 is characterized by a simpler and more compact design. In the area of base plate 12 the sealing device has a less complex design. Only one locking device is provided here.

Furthermore a temperature sensor 50 has been omitted.

In addition, housing 3 also does not have any protective webs 20 for protecting measuring tip 4. Measuring tip 4 here is designed in such a way that it tapers to a tip at front end 6 and is thus suitable for insertion into a solid material to be measured, such as meat.

Measuring module 1 is advantageously equipped with an elastic safety jacket (not shown here) for reasons of stability, tightness and hygiene.

Figure 4:
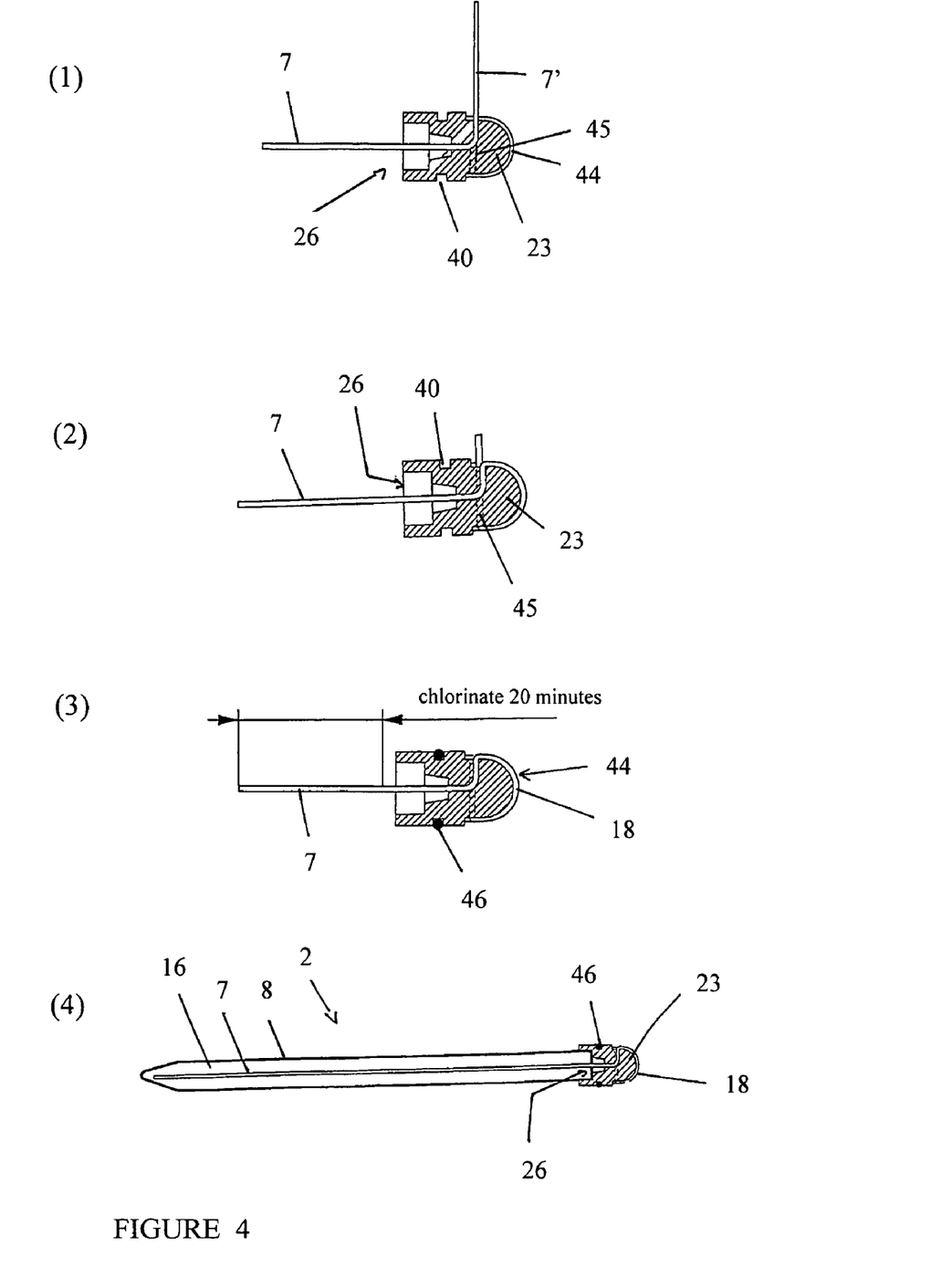
FIG. 4 shows a second method according to the present invention for manufacturing a measuring module according to FIG. 3 on the basis of subfigures (1)-(4).

FIG. 4 shows a second method according to the present invention for manufacturing a measuring module 1 according to FIG. 3 on the basis of subfigures (1)-(4). The method for manufacturing measuring module 1 corresponds here essentially to the method described with reference to FIG. 2. Therefore only a few method steps have been selected as exemplary in FIG. 4.

Method steps (1)-(4) differ from steps (1)-(5) essentially in that receptacle device 23 in FIG. 4 has a much simpler design. In particular, sealing projections 41, rubber buffer 42 and inside gasket 43 are omitted here. Only a simple O-ring 46 is provided in groove 40 here. Receptacle device 23 is therefore designed to be elastic. When glass tube 8 is inserted into recess 26, this results in frictional forces which secure glass tube 8 with respect to recess 26.

Figure 2:
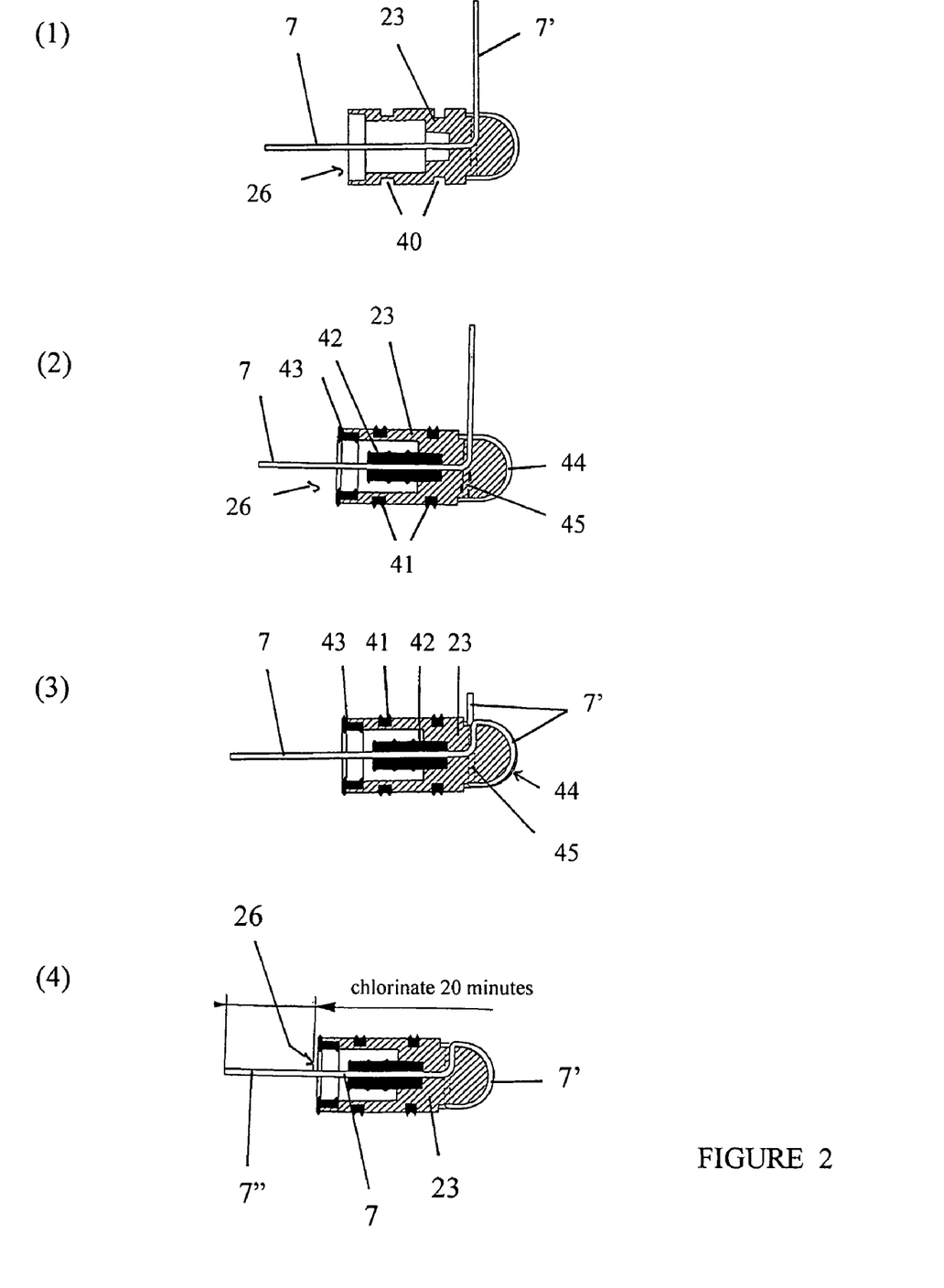
FIG. 2 shows a first method according to the present invention for manufacturing a measuring module according to FIG. 1 on the basis of subfigures (1)-(10)

In contrast to FIG. 2, the manufacture of temperature sensor 50 (steps 6 and 7) is omitted here.

In summary, it can be concluded that this novel method permits a much simpler method of manufacturing a measuring module 1 in which the previous problems associated with the risk of breaking glass tube 50 during its manufacture have been minimized despite extensive automation of the manufacturing process.

The present invention has been described here on the basis of the preceding exemplary embodiments to explain the principle of the present invention and its practical application in the best possible way, but the method according to the present invention may of course also be suitably modified.

Accordingly, other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for manufacturing a measuring probe comprising a housing and two electrodes, including the method steps:
    (a) forming a receptacle device, including providing an electrode wire sheathed with extruded plastic, the wire protruding out of the receptacle device on both ends, wherein the electrode wire is attached to the receptacle device at a first end of the electrode wire, wherein in order to form the first electrode, a glass tube is pushed over a second end of the electrode wire until the glass tube comes in contact with a recess in the receptacle device, and wherein the glass tube and receptacle device are attached to one another;
    (b) forming a base plate having a recess in the shape of the receptacle device, including providing an additional electrode wire sheathed with extruded plastic, the additional electrode wire protruding out of the base plate on both ends, wherein the additional electrode wire is attached to the base plate at an end of the additional electrode wire which protrudes out of the base plate;
    (c) providing a sheathing having a first opening in the form of the base plate and a second opening in the shape of the glass tube is provided, wherein in order to form the housing, the sheathing and base plate are sealed together; and
    (d) pushing the glass tube through the recess in the base plate until the glass tube protrudes out of an opening in the sheathing and the receptacle device comes in contact with the base plate.

2. The method as recited in claim 1, wherein to attach the electrode wire, the electrode wire is pushed by the first end of the electrode wire through a transverse through bore provided in the receptacle device, tightened, and an end protruding out of the transverse through bore is cut off.

3. The method as recited in claim 1, wherein to attach the electrode wire, the electrode wire is threaded by the first end into a receptacle means provided in at least one of the base plate and the receptacle device, and is tightened and a protruding end is cut off.

4. The method as recited in claim 1, wherein the sheathing and base plate are sealed by ultrasonic welding.

5. The method as recited in claim 4, wherein a double weld is produced.

6. The method as recited in claim 1, wherein an electrolyte liquid is added to the housing after sealing the base plate and the sheathing.

7. The method as recited in claim 1, wherein to form the first electrode an electrolyte liquid is added into the glass tube.

8. The method as recited in claim 1, wherein the receptacle device has a groove running on an outside surface of the receptacle device on an end of the receptacle device opposite the recess, with the electrode wire being placed in the groove.

9. The method as recited in claim 1, wherein the receptacle device has at least one of outside grooves and inside grooves into which an elastomer is extruded for manufacturing rubber projections to seal and secure the first electrode.

10. The method as recited in claim 1, wherein the receptacle device has a central recess into which an elastomer is extruded for producing a rubber buffer for buffering and sealing the first electrode.

11. The method as recited in claim 1, wherein a groove formed between the receptacle device and the base plate is sealed by an O-ring and a screw or a latching means.

12. The method as recited in claim 1, wherein to secure at least one of the first electrode and the second electrode, the at least one of the first electrode and the second electrode is glued or welded onto the housing or extruded with the housing.

13. The method as recited in claim 1, wherein to form a temperature sensor in the base plate a tube is covered with plastic, a heat transfer compound is packed into a tip of the tube, and then a twin cable is inserted into the interior of the tube, with the two ends of the wire protruding out of the tube being soldered to contact rods.

14. The method as recited in claim 13, wherein a recess is provided in the area of the base plate to accommodate a contact plate and the contact rods are inserted into the contact plate arranged in the recess.

15. The method as recited in claim 1, wherein parts of the electrode wire arranged inside the housing are at least partially chlorinated.

16. The method as recited in claim 1, wherein parts of the electrode wire which are accessible from outside the housing are at least partially gold plated.

17. The method as recited in claim 1, wherein at least one of the base plate, the sheathing and the receptacle device is manufactured by inserting into a mold and extruding plastic into the mold.

18. A method for manufacturing a measuring probe having first and second electrodes, comprising:
    providing a receptacle device, wherein a first electrode wire protrudes out of the receptacle device and a first end of said first electrode wire is attached to the receptacle device;
    positioning a tube over a second end of said first electrode wire until the tube comes in contact with a recess in the receptacle device;
    providing a base plate having a recess, wherein a second electrode wire protrudes out of the base plate and a first end of said second electrode wire is attached to the base plate;
    providing a sheathing having a first opening in the shape of said base plate and a second opening in the shape of said tube;
    sealing the sheathing and base plate together to form a housing; and
    pushing the tube toward the recess in the base plate, wherein the tube protrudes out of said second opening in the sheathing and the receptacle device is in contact with the base plate,
    wherein to attach said first electrode wire to said receptacle device, said first end of said first electrode wire is pushed through a transverse opening provided in the receptacle device, tightened, and a protruding end is cut off.

19. The method of claim 18, wherein the tube is made of glass.

20. The method of claim 18, wherein the first electrode wire and the second electrode wire are sheathed with extruded plastic.

21. The method as recited in claim 18, wherein to attach said first electrode wire to said receptacle device, said first electrode wire is threaded by said first end into a receptacle means provided in at least one of the base plate and receptacle device, tightened, and a protruding end is cut off.

22. The method as recited in claim 18, wherein an electrolyte liquid is added to the housing after sealing the base plate and the sheathing.

23. The method as recited in claim 18, wherein the first electrode is formed by adding an electrolyte liquid into the tube.

24. The method as recited in claim 18, wherein the receptacle device includes a groove disposed on an outside surface of the receptacle device at an end opposite the recess, and wherein said first electrode wire is disposed in said groove.

25. The method as recited in claim 18, wherein the receptacle device includes grooves into which an elastomer is extruded for manufacturing rubber projections to seal and secure the first electrode.

26. The method as recited in claim 18, wherein the receptacle device includes a central recess into which an elastomer is extruded for producing a rubber buffer for buffering and sealing the first electrode.

27. The method as recited in claim 18, wherein a groove is formed between the receptacle device and the base plate and is sealed by at least one of an O-ring, a screw and a latching means.

28. The method as recited in claim 18, wherein the first electrode and the second electrode are glued or welded onto the housing or extruded with the housing.

29. The method as recited in claim 18, further comprising a temperature sensor disposed in the base plate, wherein said temperature sensor includes a sensor tube covered with plastic, wherein a heat transfer compound is packed into a tip of the sensor tube and a twin cable is inserted into the interior of the sensor tube, and wherein two ends of a wire protruding out of the sensor tube are attached to contact rods.

30. The method as recited in claim 18, further comprising a contact plate disposed in said recess in the base plate, and wherein contact rods are inserted into the contact plate.

31. The method as recited in claim 18, wherein parts of the first and second electrode wires disposed inside the housing are at least partially chlorinated.

32. The method as recited in claim 18, wherein parts of the first electrode wire which are accessible from outside the housing are at least partially gold plated.

33. The method as recited in claim 18, wherein at least one of the base plate, the sheathing and the receptacle device is manufactured by inserting into a mold and extruding plastic into the mold.

* * * * *